United States Patent
Koseki et al.

(10) Patent No.: US 12,252,676 B2
(45) Date of Patent: Mar. 18, 2025

(54) CELL CULTURE SYSTEM

(71) Applicant: TOYO SEIKAN GROUP HOLDINGS, LTD., Tokyo (JP)

(72) Inventors: Osamu Koseki, Kanagawa (JP); Satoshi Tanaka, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 728 days.

(21) Appl. No.: 17/509,119

(22) Filed: Oct. 25, 2021

(65) Prior Publication Data
US 2022/0041965 A1 Feb. 10, 2022

Related U.S. Application Data

(63) Continuation of application No. PCT/JP2020/008608, filed on Mar. 2, 2020.

(30) Foreign Application Priority Data

Apr. 27, 2019 (JP) ................... 2019-086904

(51) Int. Cl.
*C12M 3/00* (2006.01)
*C12M 1/00* (2006.01)
(Continued)

(52) U.S. Cl.
CPC ............ *C12M 23/14* (2013.01); *C12M 23/26* (2013.01); *C12M 23/48* (2013.01); *C12M 29/14* (2013.01); *C12M 41/48* (2013.01)

(58) Field of Classification Search
None
See application file for complete search history.

(56) References Cited

U.S. PATENT DOCUMENTS 9,909,090 B2    3/2018  Tanaka et al.
2010/0317102 A1  12/2010  Suzuki et al.
(Continued)

FOREIGN PATENT DOCUMENTS

EP    1978089 A1    10/2008
JP    H2-255079 A   10/1990
(Continued)

OTHER PUBLICATIONS

Extended European Search Report (EESR) issued in European Patent Application No. 20798171.3, dated Jan. 16, 2023 (13 pages).
(Continued)

*Primary Examiner* — Neil N Turk
(74) *Attorney, Agent, or Firm* — Nakanishi IP Associates, LLC

(57) ABSTRACT

A cell culture system includes a culture bag made of a flexible packaging material and having a plurality of ports, a medium container that stores a medium to be transferred to the culture bag, and a control part that controls the supply of the medium, tubular members are connected to the respective ports to circularly connect the culture bag and the medium container through the tubular members, the tubular member connected to a first port of the plurality of ports is provided with first supply unit (e.g., pump), and the tubular member connected to a second port of the plurality of ports is provided with second supply unit (e.g., pump), and the control part controls the operation of at least the first supply unit or the second supply unit to circulate the medium in the culture bag and the medium container.

9 Claims, 12 Drawing Sheets

(51) Int. Cl.
*C12M 1/34* (2006.01)
*C12M 1/36* (2006.01)

(56) References Cited

U.S. PATENT DOCUMENTS

| | | |
|---|---|---|
| 2012/0264210 A1 | 10/2012 | Bontinck et al. |
| 2012/0295289 A1 | 11/2012 | Zandstra et al. |
| 2013/0344597 A1 | 12/2013 | Suzuki et al. |
| 2014/0051167 A1 | 2/2014 | Nankervis et al. |
| 2014/0335608 A1 | 11/2014 | Tanaka et al. |
| 2016/0194589 A1 | 7/2016 | Liderfelt et al. |
| 2016/0215257 A1 | 7/2016 | Davis et al. |
| 2016/0274111 A1 | 9/2016 | Zandstra et al. |
| 2016/0340633 A1 | 11/2016 | Davis et al. |
| 2017/0044477 A1 | 2/2017 | Gebauer et al. |
| 2017/0073624 A1 | 3/2017 | Stankowski et al. |
| 2017/0253847 A1 | 9/2017 | Koseki et al. |
| 2018/0002667 A1 | 1/2018 | Keskar et al. |
| 2018/0127696 A1 | 5/2018 | Takeuchi et al. |
| 2018/0127704 A1 | 5/2018 | Sasayama et al. |
| 2020/0087605 A1 | 3/2020 | Gebauer et al. |
| 2020/0199508 A1 | 6/2020 | Suenaga et al. |

FOREIGN PATENT DOCUMENTS

| | | |
|---|---|---|
| JP | 5892216 B1 | 3/2016 |
| JP | 2018-183150 A | 11/2018 |
| JP | 2019-000045 A | 1/2019 |
| WO | 2013/114845 A1 | 8/2013 |
| WO | 2015/034416 A1 | 3/2015 |
| WO | 2015/180908 A1 | 12/2015 |
| WO | 2016/113369 A1 | 7/2016 |
| WO | 2016/190312 A1 | 12/2016 |
| WO | 2016/190314 A1 | 12/2016 |
| WO | 2018/002091 A1 | 1/2018 |

OTHER PUBLICATIONS

Office Action issued in Japanese Patent Application No. 2019-086904 dated Mar. 7, 2023, with English Translation (10 pages).
Office Action issued in Japanese Patent Application No. 2019-086904 mailed on Sep. 5, 2023, with English Translation (16 pages).
Office Action issued in Chinese Patent Application No. 202080031577.2, dated Jul. 24, 2023, with English Translation of Substantial Part (27 pages).
International Search Report issued in PCT/JP2020/008608 mailed on May 26, 2020 with English Translation (7 pages).

(a)

(b)

(a)

(b)

(c)

CELL CULTURE SYSTEM

TECHNICAL FIELD

The present invention relates to a cell culture technique, in particular, relates to a technique of controlling the supply of a medium to a culture bag that is used to culture cells.

BACKGROUND ART

In recent years, it is required to efficiently culture a large amount of cells, tissues, etc., in an artificial environment in the fields of pharmaceutical production, gene therapy, regenerative medicine, immunotherapy, and the like.

Under such circumstances, in order to culture a large amount of cells, various methods for automatically culturing cells in a closed system using culture bags made of a flexible packaging material are being studied. The development of cell culture systems to realize such methods is underway.

In a cell culture system, it is desirable to perform supply control (transfer control) to supply an appropriate amount of medium to culture bags in an appropriate timing.

As medium supply control, for example, a medium bag for supplying a medium is connected to a culture bag by a tube, the tube is provided with a pump, and the pump is operated to control the supply of the medium from the medium bag to the culture bag.

Specifically, in the cell culture system described in Patent Document 1, a medium bag and a plurality of culture bags are connected by a tube, a pump is attached to the tube, and the supply of the medium from the medium bag to the culture bags is controlled by the pump.

CITATION LIST

Patent Literature

Patent Document 1: JP-B-5892216
Patent Document 2: WO2016/190312 pamphlet
Patent Document 3: WO2016/190314 pamphlet

SUMMARY OF INVENTION

Technical Problem

The cell culture system described in Patent Document 1 uses only one pump to thereby eliminate the need for synchronization when a plurality of pumps are connected in series, and is intended to reduce the work of attaching pumps to tubes.

On the other hand, when a plurality of pumps are connected in series, it is possible to synchronize these pumps by finely controlling their operation.

In particular, a plurality of ports are formed in a culture bag, tubes connected to these ports are each provided with a pump, and these pumps are controlled at the same time, thereby making it possible to finely control the inflow and discharge of the medium to the culture bag.

Accordingly, the present inventors have developed a cell culture system in which a culture bag comprising a plurality of ports is circularly connected to a medium bag through tubes, and the tubes connected to the respective ports are each provided with a pump, and the operation of these pumps is controlled, thereby making it possible to control the supply of the medium to the culture bag.

Since such a cell culture system can finely control the inflow and discharge of the medium from the medium bag to the culture bag, for example, the medium bag is filled with a necessary medium from the start to the end of culture, and this medium is supplied to the culture bag, whereby cell culture can be performed automatically.

Moreover, in the cell culture system, it is desirable to grasp the state of the culture bag and to control the supply of the medium optimally for that state.

For example, conventionally, a weight sensor was used to measure the combined weight of a culture bag, a holding plate holding the culture bag or the like, and the weight of the medium was calculated based on the combined weight to of the medium to the culture bag.

In contrast, the liquid thickness of the medium filled in the culture bag (the width of the gap between the upper surface film and the lower surface film of the culture bag) is confirmed as the state of the culture bag, and supply control is performed depending on the state, thereby making it possible to perform more various controls in cell culture.

For example, when a culture bag having a culture part with many recesses is used to culture spheres (spheroids, aggregates) or organoids in the recesses, the medium is supplied after the liquid thickness of the medium is adjusted to a size that does not allow the movement of the spheres, thereby making it possible to prevent the spheres from moving between the recesses.

Accordingly, the present inventors detected the liquid thickness of a medium filled in a culture bag using a length measurement sensor, and controlled the operation of pumps based on the detection information, thereby making it possible to control the supply of the medium and to control the liquid thickness of the medium.

Measurement using a weight sensor is generally a load cell type. Since it was necessary to load the total weight of the culture bag and the holding plate on the minute point of the load cell, there were problems that fixation was difficult and it was vulnerable to impact. In addition, weight sensors were vulnerable to temperature characteristics, such as low temperatures, and it was necessary to attach them evenly at multiple locations, which caused a problem that attachment was difficult. In addition, when there was a pipe, such as a tube, the tension of the tube was applied to the weight sensor due to contact with other housings through the tube, resulting in errors in the measured values.

An example of a technique related to control of the supply of a medium to a culture bag is the culture device described in Patent Document 2. In this culture device, a distance sensor is disposed on a spacer to be able to grasp a state in which the distance between a holding plate and the spacer is equal to or larger than a certain level. However, in this culture device, the liquid thickness of the medium in the culture bag is not detected, and the liquid thickness of the medium is not controlled.

Further, in the culture device described in Patent Document 3, the weight of a culture bag and a holding part thereof is detected using a weight detection part. However, in this culture device, the liquid thickness of the medium in the culture bag is not detected, and the liquid thickness of the medium is not controlled.

In addition, it is desirable for the cell culture system to keep the medium in the culture bag uniform in order to obtain cells and spheres with a uniform size.

Accordingly, the present inventors made the above cell culture system rotatable, thereby making it possible to rotate the culture bag to stir the medium, and to keep the medium uniform in the culture bag.

According to such a cell culture system, when adherent cells are cultured by attaching them to the culture part of the culture bag, the adherent cells are attached to the lower surface side of the culture bag, the culture bag is then inverted upside down to attach the adherent cells to the original upper surface side (new lower surface side) of the culture bag, and the cells are cultured by inverting the culture bag upside down, as appropriate, thereby making it possible to double the culture area.

In addition, after controlling the liquid thickness of the medium to a size that does not allow the movement of spheres, the culture bag is inverted upside down, thereby making it possible to discharge only the medium while holding the spheres in recesses formed in the culture part of the culture bag.

Furthermore, in order to enable mass-culture of cells using such a cell culture system, it is desirable to increase the culture area by using a plurality of culture bags.

Accordingly, the present inventors connected a plurality of culture bags in parallel, connected them to a common medium bag, provided a pump in each tube connected to each culture bag, and controlled the operation of these pumps, thereby making it possible to separately control the supply (control the transfer) of the medium to each culture bag.

The present invention was made in view of the above circumstances. An object of the present invention is to provide a cell culture system that can finely control the inflow and discharge of a medium from a medium bag to a culture bag.

Solutions to Problem

In order to achieve the above object, the cell culture system of the present invention is configured to comprise a culture bag made of a flexible packaging material and having a plurality of ports, a medium container that stores a medium to be transferred to the culture bag, and a control part that controls a supply of the medium, tubular members are connected to the respective ports to circularly connect the culture bag and the medium container through the tubular members, the tubular member connected to a first port of the plurality of ports is provided with first supply means, and the tubular member connected to a second port of the plurality of ports is provided with second supply means, and the control part controls an operation of at least the first supply means or the second supply means to circulate the medium in the culture bag and the medium container.

Advantageous Effects of Invention

According to the present invention, it is possible to provide a cell culture system that can finely control the inflow and discharge of a medium from a medium bag to a culture bag.

DESCRIPTION OF EMBODIMENTS

Hereinafter, embodiments of the cell culture system of the present invention will be described in detail. Note that the present invention is not limited to the specific contents of the following embodiments.

First Embodiment

First, the first embodiment of the cell culture system according to the present invention will be described with reference to FIGS. 1 to 3.

The cell culture system of the present embodiment comprises a culture bag made of a flexible packaging material and having a plurality of ports, a medium container that stores a medium to be transferred to the culture bag, and a control part that controls the supply of the medium, tubular members are connected to the respective ports to circularly connect the culture bag and the medium container through the tubular members, the tubular member connected to a first port of the plurality of ports is provided with first supply means, and the tubular member connected to a second port of the plurality of ports is provided with second supply means, and the control part controls the operation of at least the first supply means or the second supply means to circulate the medium in the culture bag and the medium container.

Figure 1:
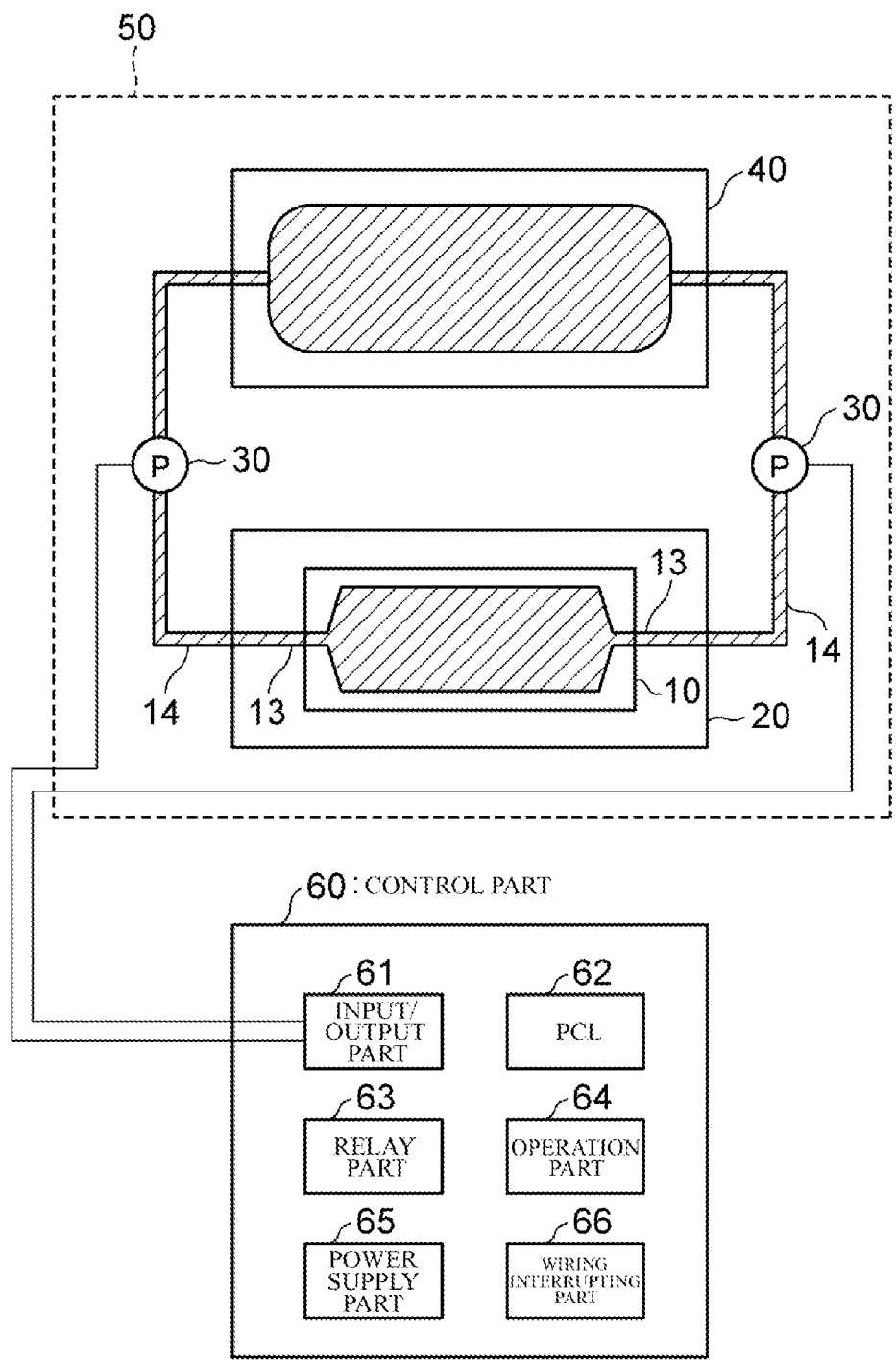
FIG. 1 is an explanatory diagram illustrating the structure of a cell culture system according to a first embodiment of the present invention.

Specifically, as shown in FIG. 1, for example, a culture bag 10 having two ports 13 and a medium bag 40 are circularly connected by tubular members 14, such as tubes, the tubular members 14 connected to each of the two ports 13 are each provided with supply means 30, such as a pump, and the operation of these supply means 30 is controlled by a control part 60.

In the present embodiment, the culture bag 10 is stored in a culture bag storage part 20, and the culture bag storage part 20, the medium bag 40, the tubular members 14, the supply means 30, etc., are combined to form a single culture unit 50 using one culture bag 10.

Figure 2:
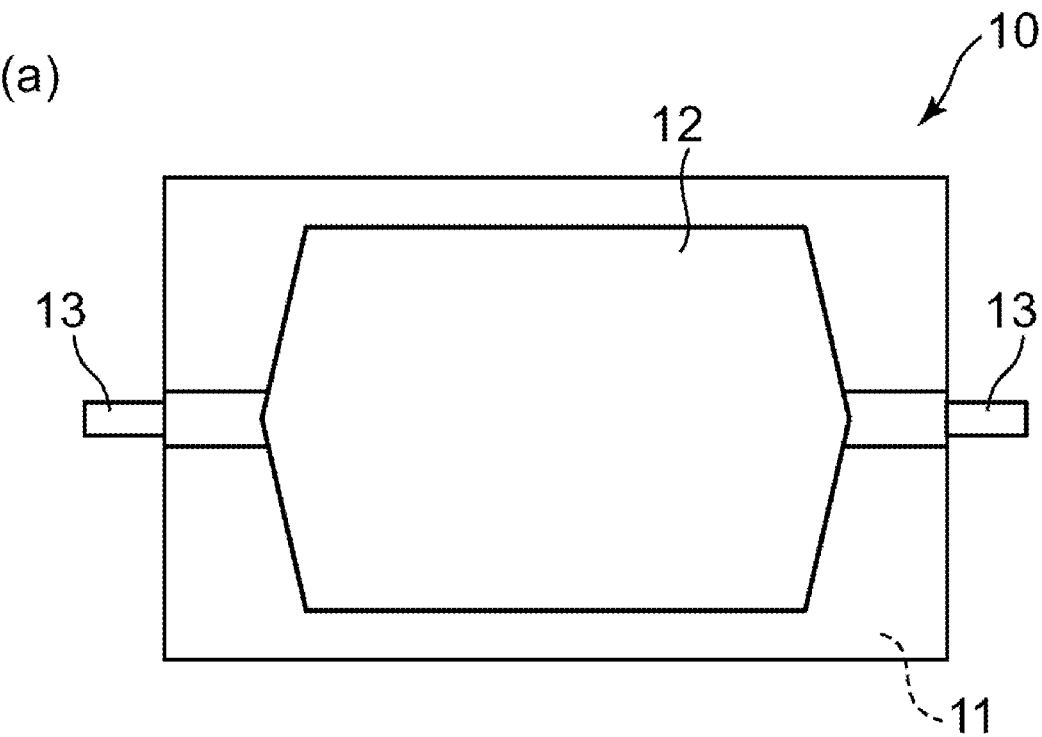
FIG. 2 is schematic diagrams illustrating the outline of a culture bag used in the cell culture system according to each embodiment of the present invention; (a) is a plan view, and (b) is a front view.
Figure 2:
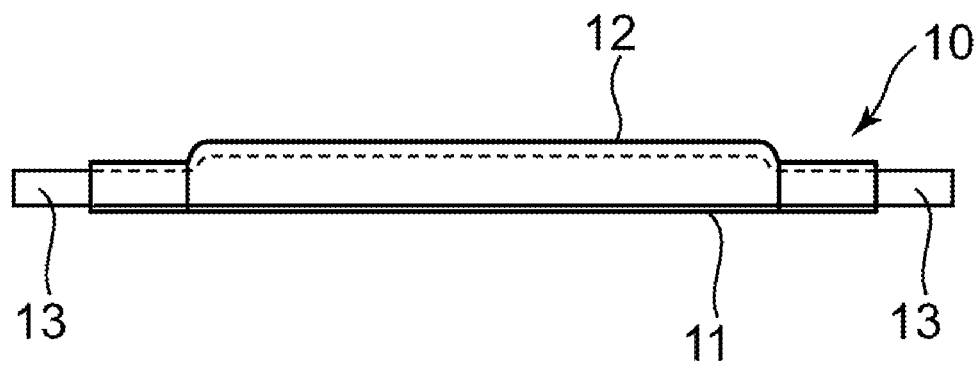

The culture bag 10 is made of a flexible packaging material, and can be formed by bonding together the peripheral portions of a bottom side film 11 (lower surface film) and a top plate side film 12 (upper surface film) by heat sealing or the like, as shown in FIG. 2. Further, the culture bag 10 is provided with a plurality of (two in FIG. 2) ports 13. These ports 13 are connected to tubular members, and supply means provided in the tubular members are used to supply the medium, such as injection of the medium into the culture bag 10 and discharge of the medium from the culture bag 10, through the ports 13.

Then, the width of the gap between the bottom side film 11 and the top plate side film 12 (liquid thickness) changes depending on the amount of medium injected into the culture bag 10.

When the culture bag 10 is provided with two ports, it is preferable that the first port and the second port are arranged point symmetrically with respect to the center of a culture part at both ends of the culture bag 10 so that the medium in the culture bag 10 can be sufficiently exchanged.

The culture part is a bottom surface portion in the culture bag 10 that comes into contact with the medium, and the center of the culture part refers to the center of the horizontal plane of the culture part. The horizontal plane of the culture part is parallel to the upper end surface of the culture part.

The surface of the bottom side film 11 in the culture bag 10 is used as a culture part for culturing cells or spheres. In the culture part of the bottom side film 11, a plurality of recesses are formed to store the culture target, such as cells or spheres, as shown in FIG. 3. The formation of such recesses makes it possible to suitably form and culture spheres. The arrangement of the recesses in the culture part 11 can be, for example, staggered or grid.

In FIG. 2, the bottom side film 11 of the culture bag 10 is plane, and the top plate side film 12 swells upward with the inflow of the medium. Due to the culture bag 10 configured as described above, the bottom surface of all of the recesses can be brought into contact with the mounting surface, and the liquid thickness of the medium in the culture bag 10 can be made almost uniform. Therefore, it is possible to reduce the difference in the proliferation of the culture target and the variation in the number of cells at the time of cell seeding.

The shape of the culture bag 10 used in the cell culture system of the present embodiment is not limited to the one shown in FIG. 2 (b). The culture bag can also be formed by bonding together a bottom side film 11 and a top plate side film 12 of the same shape by heat sealing or the like.

Further, in FIG. 2 (a), the shape of the culture bag 10 near the port of the culture part is formed at an angle to the port, which facilitates the flow of the medium to the port. However, the shape of the culture part is not limited to such a shape, and the culture part can be formed into a rectangular shape, such as a square.

Figure 3:
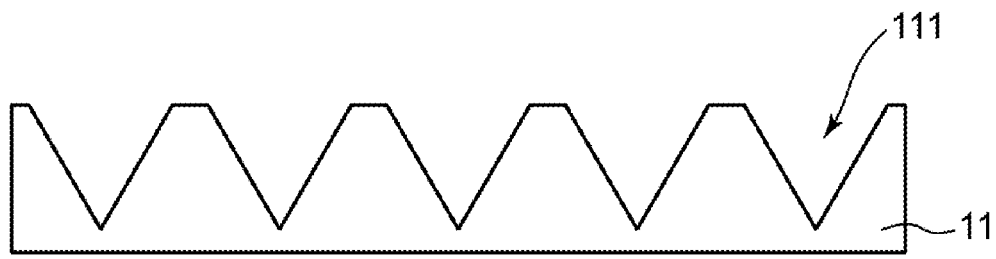
FIG. 3 is schematic diagrams illustrating a part of a culture part provided with various recesses in the culture bag used in the cell culture system according to each embodiment of the present invention.
Figure 3:
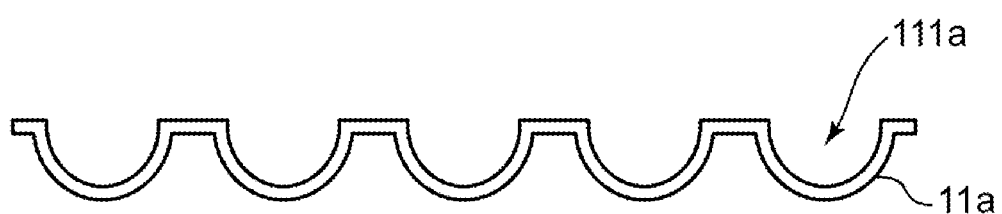
Figure 3:
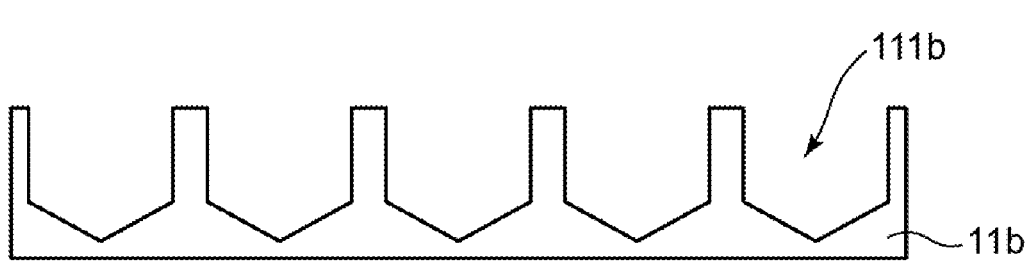

The shape of the recesses formed in the culture part of the bottom side film 11 can be pyramidal such as conical or square pyramidal, as shown in FIG. 3 (a), or hemispherical or rounded, as shown in FIG. 3 (b).

Further, the shape of the recesses formed in the culture part of the bottom side film 11 is also preferably such that at least a part of the side wall is formed substantially vertically, as shown in FIG. 3 (c). In these recesses, the length in the vertical direction of the substantially vertical part of the side wall is longer than half of the maximum diameter of the culture target. In addition, the shape of the region with a substantially vertical side wall in the recesses can be, for example, a cylindrical or square column.

Due to the recesses in the culture bag 10 in such a shape, when the medium is supplied from the port 13 into the culture bag 10 even at a flow rate of 1 ml/min or more, it is possible to prevent the culture target from jumping out of the recesses and moving to other recesses.

When the culture target is spheres, the depth of the recesses is preferably 50 to 500 µm. This is because if the depth of the recesses is larger than 500 µm, even when the medium is supplied to the culture bag 10, it may be difficult to sufficiently replace the medium in the recesses, and bags with recesses deeper than 500 µm are more difficult to process. The size of spheres is about 50 µm to 100 µm for small spheres, and about 200 µm to 300 µm for large spheres.

The shape of the bottom of the recesses is not particularly limited. When the culture target is spheres, the shape of the bottom of the recesses is preferably pyramidal, hemispherical, or rounded so as to facilitate the aggregation of single cells and to suitably form spheres.

When the culture target is single cells, the depth of the recesses is preferably 5 to 50 µm. This is because the size of single cells is about 6 µm to 15 µm, and many of them have a size of about 10 µm.

The shape of the openings of the recesses is not particularly limited, and can be circular or rectangular, such as square. The width of the openings of the recesses can be suitably set according to the size of the culture target.

For example, when the culture target is spheres, the lower limit of the diameter of the circle or inscribed circle of the opening of each recess may be 60 µm or more, 70 µm or more, 80 µm or more, 90 µm or more, 100 µm or more, 110 µm or more, 120 or more, 150 µm or more, or the like. Further, the upper limit of the diameter of the circle or inscribed circle of the opening of each recess may be 1 mm or less, 900 µm or less, 800 µm or less, 700 µm or less, 500 µm or less, or the like.

When the culture target is single cells, the lower limit of the diameter of the circle or inscribed circle of the opening of each recess may be 5 µm or more, 6 µm or more, 8 µm or more, or the like. Further, the upper limit of the diameter of the circle or inscribed circle of the opening of each recess may be 50 µm or less, 40 µm or less, 30 µm or less, or the like.

The "cells" in the present specification include not only single cells and spheres, but also organoids and tissues formed from them.

As the material of the culture bag 10 used in the cell culture system of the present embodiment, polyolefin-based resins, such as polyethylene and polypropylene, can be suitably used. Examples thereof include polyethylene, ethylene-α-olefin copolymers, ethylene-vinyl acetate copolymers, ionomers using ethylene-acrylic acid or -methacrylic acid copolymers and metal ions, and the like. Other examples include polyolefins, styrene-based elastomers, polyester-based thermoplastic elastomers, silicone-based thermoplastic elastomers, silicone resins, and the like. Still other examples include silicone rubber, flexible polyvinyl chloride resins, polybutadiene resins, ethylene-vinyl acetate copolymers, chlorinated polyethylene resins, polyurethane-based thermoplastic elastomers, polyester-based thermoplastic elastomers, silicone-based thermoplastic elastomers, styrene-based elastomers (e.g., SBS (styrene-butadiene-styrene), SIS (styrene-isoprene-styrene), SEBS (styrene-ethylene-butylene-styrene), and SEPS (styrene-ethylene-propylene-styrene)), polyolefin resins, fluorine-based resins, and the like.

Moreover, the culture part of the bottom side film 11 is preferably subjected to low-adhesion surface coating so that the spheres and single cells do not adhere thereto. Specifically, it is preferable to apply a cell adhesion inhibitor (cell adhesion-reducing agent).

Usable examples of cell adhesion inhibitors include phospholipid polymers, polyvinyl alcohol derivatives, phospholipid-polymer complexes, polyhydroxyethyl methacrylate, polyvinyl alcohol, agarose, chitosan, polyethylene glycol, albumin, and the like. These can be used in combination.

Further, usable examples of the material of the port 13 in the culture bag 10 include thermoplastic resins, such as polyethylene, polypropylene, vinyl chloride, polystyrene-based elastomers, and FEP.

Moreover, usable examples of the material of the tubular member 14 include silicone resins, flexible polyvinyl chloride resins, polybutadiene resins, ethylene-vinyl acetate copolymers, polyurethane-based thermoplastic elastomers, polyester-based thermoplastic elastomers, silicone-based thermoplastic elastomers, styrene-based elastomers (e.g., SBS (styrene-butadiene-styrene), SIS (styrene-isoprene-styrene), SEBS (styrene-ethylene-butylene-styrene), and SEPS (styrene-ethylene-propylene-styrene)), polyolefin resins, fluorine-based resins, and the like.

The culture bag storage part 20 comprises a pedestal on which the culture bag 10 is placed, a pressing member that presses the culture bag 10 against the pedestal to thereby uniformize the liquid thickness in the culture bag 10, a top plate part provided to face the pressing member, and a support mechanism that supports the pressing member movably in a vertical direction with respect to the top plate part.

Such a culture bag storage part will be described in detail in the second embodiment, described later.

It is also preferable that the cell culture system of the present embodiment is configured to comprise a culture unit 50 having a culture bag storage part 20 comprising a pedestal on which the culture bag 10 is placed, a pressing member that presses the culture bag 10 against the pedestal to thereby uniformize the liquid thickness in the culture bag 10, a top plate part that is provided to face the pressing member, and a support mechanism that supports the pressing member movably in a vertical direction with respect to the top plate part; a medium container storage part (not shown) that stores the medium bag 40; and a storage part (not shown) that stores each supply means 30 and the tubular members 14 that connect the culture bag 10 and the medium bag 40.

The cell culture system of the present embodiment configured as described above makes it possible to suitably control the supply of the medium in the culture bag 10.

The supply means 30 are provided in the tubular members 14 that connect the culture bag 10 and the medium bag 40. As the supply means 30, it is preferable to use pumps, such tube pumps, that can supply liquid at a low speed and with high accuracy.

With such pumps, filling of the medium from the medium bag 40 to the culture bag 10, and discharge of the medium from the culture bag 10 to the medium bag 40 can be suitably controlled by a simple configuration.

As the supply means 30, tube pumps can be used in combination with solenoid valves, such as pinch valves or needle type flow control valves, or diaphragm pumps and solenoid valves can be used in combination, or supply means by the hydraulic head difference (self-weight), pressure, or the like can also be used in combination.

The medium bag 40 is used as a medium supply bag that circulates and supplies the medium to the culture bag 10.

In the present embodiment, the medium container is not limited to the medium bag 40 made of a flexible packaging material. A rigid container can also be used as the medium container.

The control part 60 (control unit) is not particularly limited as long as it can control the operation of the supply means 30 based on the preset information. The control part can be configured to comprise an input/output part 61 (input/output unit), PLC (programmable logic controller) 62, a relay part 63 (relay), an operation part 64 (touch panel etc.), a power supply part 65 (stabilized power supply etc.), and a wiring interrupting part 66 (breaker). Such a configuration may also be realized by a microcontroller or a computer.

The input/output part 61 is connected to the two supply means 30 by wiring cords. Desired control contents are previously programmed and stored in PLC 62. Then, the operation of these supply means 30 is controlled based on instruction information from PLC 62.

For example, first information corresponding to a first state in which the liquid thickness of the medium is zero is stored by PLC 62 in the control unit 60, second information is calculated by adding a predetermined amount of change to the first information, and the operation of the supply means 30 is controlled based on the second information, whereby the liquid thickness of the medium can be controlled to a second state corresponding to the second information. The first information and the second information can be, for example, voltage, current, transistor output, or the liquid thickness of the medium.

Since such a cell culture system of the present embodiment can finely control the inflow and discharge of the medium from the medium bag 40 to the culture bag 10, for example, the medium bag is filled with a necessary medium from the start to the end of culture, and this medium is supplied to the culture bag 10, whereby cell culture can be performed automatically.

Second Embodiment

Next, the second embodiment of the cell culture system according to the present invention will be described with reference to FIGS. 4 to 9.

The cell culture system of this embodiment is different from the cell culture system of the first embodiment in that it comprises a detection part that measures a change occurring in response to a change in the amount of medium in the culture bag, and the operation of at least the first supply means or the second supply means is controlled based on detection information input from the detection part. The other structures can be the same as those of the first embodiment, except for the points described below.

The change occurring in response to a change in the amount of medium in the culture bag is preferably displacement of the position of a member, and a length measuring sensor is preferably used as the detection part.

Figure 4:
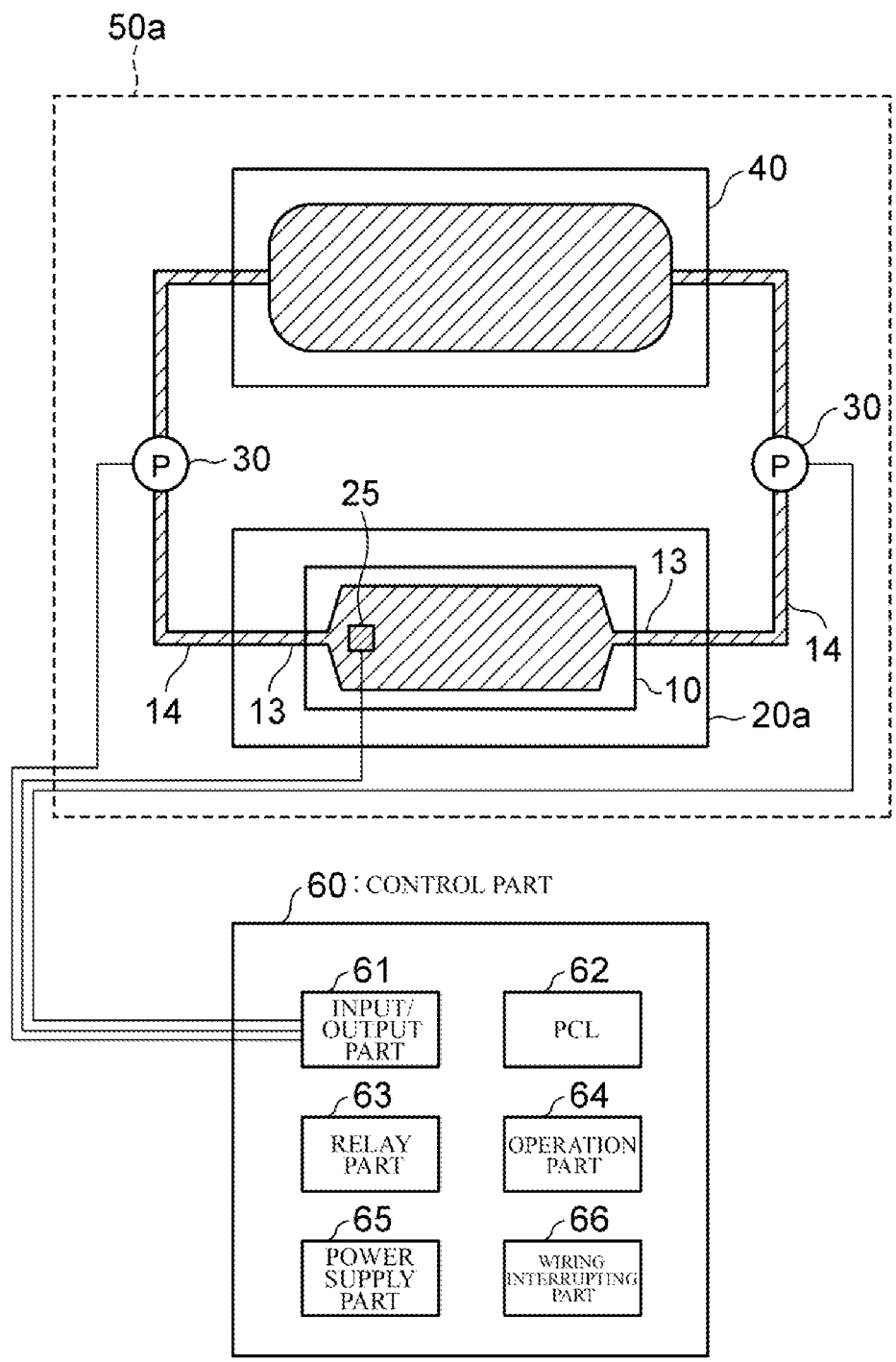
FIG. 4 is an explanatory diagram illustrating the structure of a cell culture system according to a second embodiment of the present invention.

Specifically, as shown in FIG. 4, the cell culture system of the present embodiment comprises a length measurement sensor 25 in a culture bag storage part 20a, and the operation of the supply means 30 can be controlled based on detection information from the length measurement sensor 25.

As the length measurement sensor 25, various types of sensors, such as electromagnetic induction type, laser type, ultrasonic type, and magnetic type, can be used. There are two types of sensors, i.e., analog (linear) type and switch type, and it is preferable to use an analog type sensor, which is a regular measurement type.

When using an electromagnetic induction type length measurement sensor or the like, it is preferable to attach a metal member to the position to be measured. This is because the sensitivity of the sensor can be improved by doing so. When using a laser type or ultrasonic type length measurement sensor, measurement can be carried out without attaching a metal member to the position to be measured.

Specifically, when using an analog proximity sensor (electromagnetic induction type, measurement distance: 1 to 6 mm, produced by Sensatec Co., Ltd., MDA-C5) as the length measurement sensor 25, the output voltage (or output current) is roughly proportional to the measurement distance. Within this measurement distance range, a change of 0.01 mm of the liquid thickness (the liquid thickness of the medium in the culture bag) can be detected for every 0.01 V output voltage.

For example, when using a culture bag having a culture part with a horizontal plane area of 50 $cm^2$, the amount of medium with a liquid thickness of 0.01 mm is 0.05 ml. In this case, when the supply speed is 2 ml/min, the medium can be supplied for 1.5 seconds, and the liquid thickness can be increased or decreased by 0.01 mm. When the supply speed is 0.5 ml/min, the medium can be supplied for 6 seconds, and the liquid thickness can be increased or decreased by 0.01 mm.

Further, the use of an analog distance sensor (electromagnetic induction type, measurement distance: 0 to 12 mm, produced by Fuji Electric FA Components & Systems Co., Ltd., PE2-LA10D) as the length measurement sensor 25 allows the control up to a liquid thickness of larger than about 8 mm, for example.

When the liquid thickness is directly measured using the length measurement sensor 25, for example, the length measurement sensor 25 is disposed on a pedestal on which the culture bag is placed, a metal member is disposed on a pressing member, and the distance to the metal member can be measured by the length measurement sensor 25.

In this case, the liquid thickness can be obtained by multiplying the output voltage of the length measurement sensor by a predetermined coefficient, and subtracting the thickness of the film etc.

Further, as described later, the length measurement sensor 25 is disposed on a top plate part that supports a pressing member, a metal member is disposed on the pressing member, and the distance to the metal member can be measured by the length measurement sensor 25.

In this case, the liquid thickness can be obtained by multiplying the output voltage of the length measurement sensor 25 by a predetermined coefficient to calculate the distance from the length measurement sensor 25 to the metal member, and subtracting the distance calculated above, the thickness of the metal member, the height of the pressing member, and the thickness of the film from the distance from the upper surface of the pedestal on which the culture bag is placed to the lower surface of the length measurement sensor 25.

Further, the change occurring in response to a change in the amount of medium in the culture bag can be a change in the weight of the culture bag housing part 20a on which the culture bag 10 is placed, and a weight sensor can be used as the detection part. Then, it is also possible to calculate the liquid thickness of the medium based on the change in weight by the control part 60, and to control the operation of the supply means based on this liquid thickness.

That is, it is also possible to calculate the liquid thickness by subtracting the weight at the time when the liquid thickness in the culture bag 10 is zero from the weight at the time of measurement to convert it into a volume, and dividing this volume by the area of the horizontal plane of the culture part, and to control the operation of the supply means based on this liquid thickness.

In the culture bag storage part 20a of the present embodiment, as shown in FIGS. 5 to 9, top plate support parts 22 are erected at the four corners of a pedestal 21, and a top plate part 23 is fixed to the top plate support parts 22. Guide pins 273 are provided on the periphery of the top plate part 23, and penetrate through guide holes provided in a mounting part 272 of a pressing member 27. The pressing member 27 is provided movably in the vertical direction along the guide pins 273.

Further, the top plate part 23 is provided with a top plate opening 231 so that the inside of the culture bag housing part 20a can be visually confirmed through the top plate opening 231.

Permanent magnets 26 are provided at the four corners of the top plate part 23 as energizing means for downward energizing the pressing member 27, and permanent magnets 2721 are provided as energizing means in the mounting part 272 at positions corresponding to the permanent magnets 26. These permanent magnets are arranged so that the same pole sides face each other. Due to the repulsive force acting between the permanent magnets 26 and the permanent magnets 2721, the pressing part 271 of the pressing member 27 can move in the vertical direction while vertically pressing the top plate side film 12 of the culture bag 10.

Energizing means are not limited to permanent magnets. The energizing means may be omitted, and the pressing member 27 may be moved up and down with respect to the top plate side film 12 by the self-weight of the pressing member 27.

The pressure member 27 is dimensioned so that the bottom surface of the pressing part 271 is positioned on the inner side of the culture part in the culture bag 10. That is, the shape of the horizontal plane of the pressing member 271 is the same as the shape of the horizontal plane of the culture part in the culture bag 10, and the pressing member 271 presses only the inside of the area of the culture part.

Thus, when the culture bag 10 is pressed by the pressing member 27, the occurrence of undulations of the top plate side film 12 can be suppressed. As a result, while the medium is injected or discharged, the top plate side film 12 is kept parallel to the mounting surface of the pedestal 21, and the liquid thickness of the medium in the culture bag 10 becomes uniform.

The pressing member 27 may be made of, for example, a synthetic resin such as polycarbonate, or may be formed by glass. In addition, it is preferable that part or all of the pressing member 27 is transparent so that the progress of the culture and the state of the culture target can be confirmed.

Figure 5:
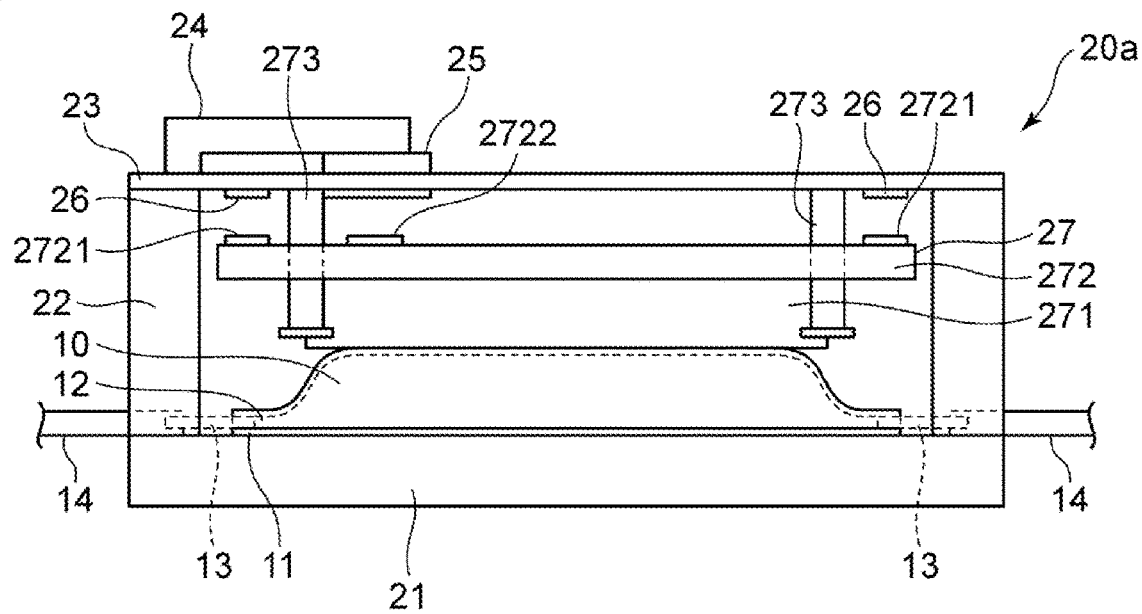
FIG. 5 is a front view illustrating the outline of a culture bag storage part used in the cell culture system according to the second embodiment of the present invention, and showing a state in which a medium is enclosed in a culture bag.
Figure 6:
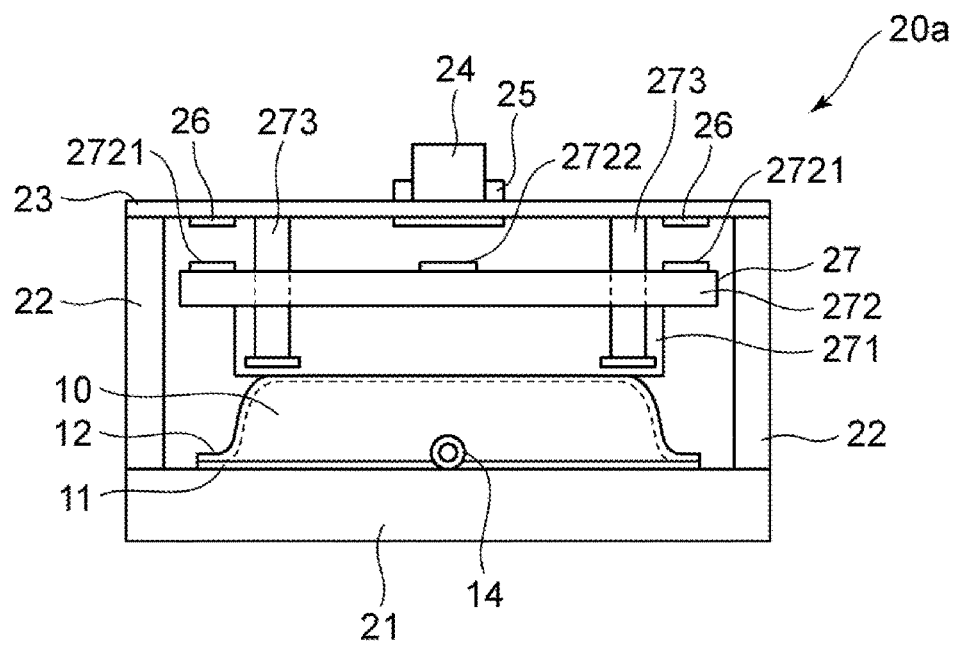
FIG. 6 is a left-side view illustrating the outline of a culture bag storage part used in the cell culture system according to the second embodiment of the present invention, and showing a state in which a medium is enclosed in a culture bag.
Figure 7:
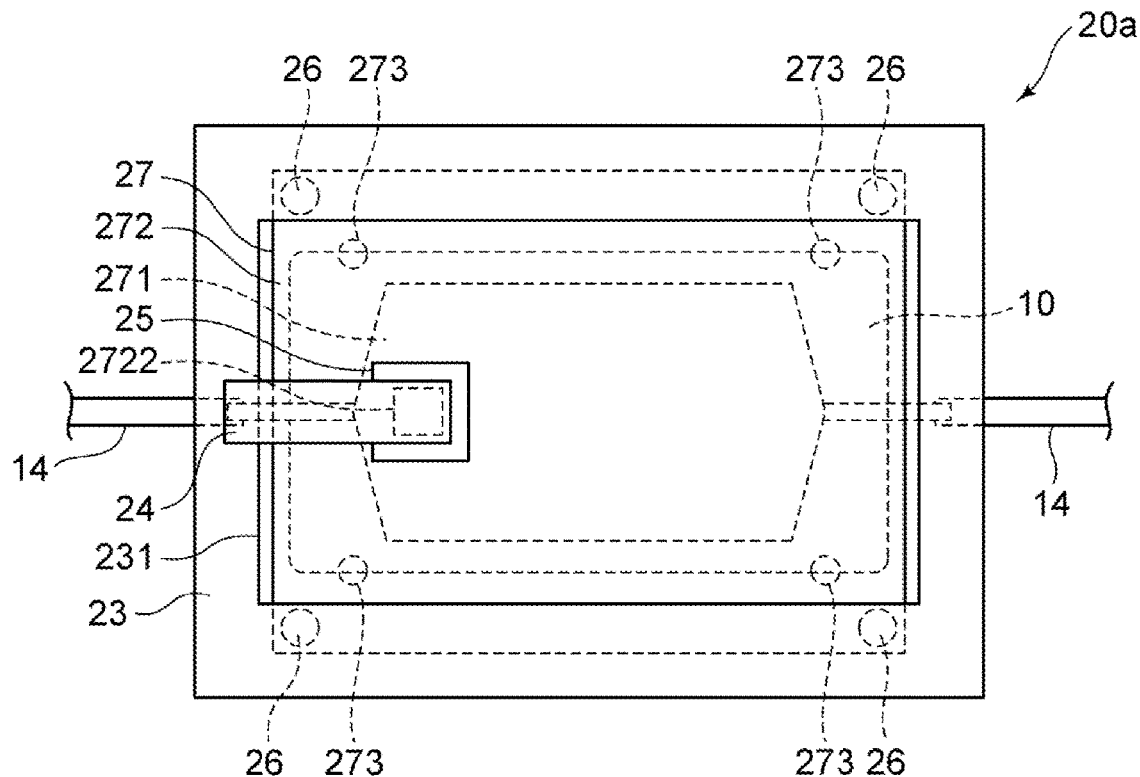
FIG. 7 is a plan view illustrating the outline of a culture bag storage part used in the cell culture system according to the second embodiment of the present invention.

When the medium is filled in the culture bag 10, the pressing member 27 is pushed up by the culture bag 10, as shown in FIGS. 5 and 6.

On the other hand, when the medium is discharged from the culture bag 10 by the supply means 30 disposed in the tubular members 14 through the tubular members 14 connected to the ports 13 of the culture bag 10, the liquid thickness of the medium in the culture bag 10 decreases accordingly, and the pressing member 27 descends accordingly.

Figure 8:
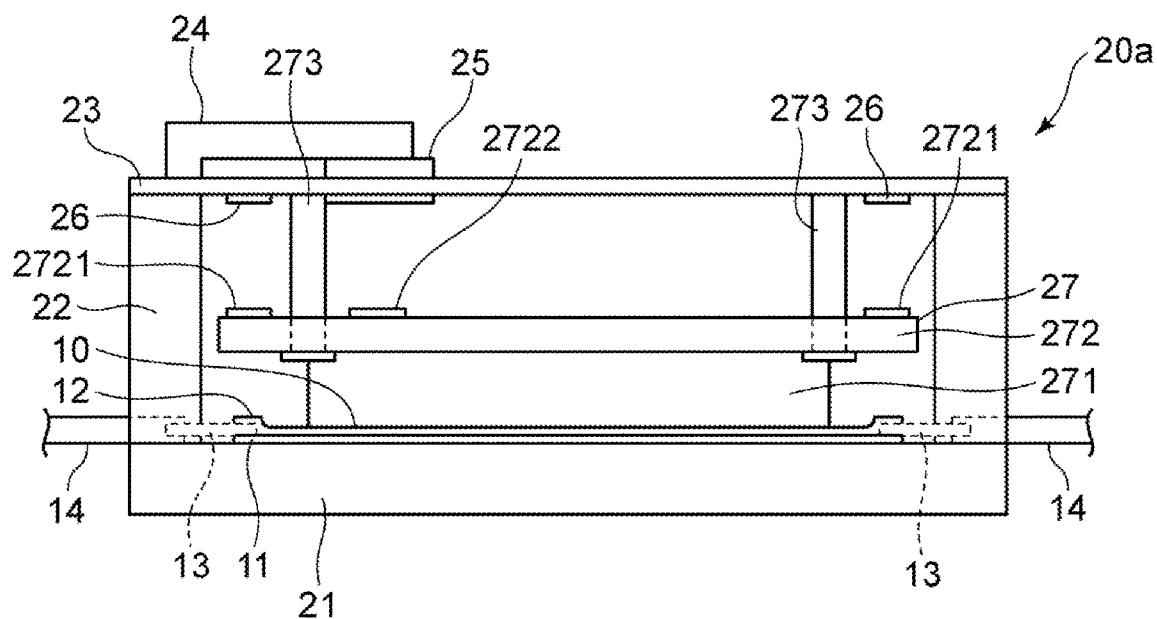
FIG. 8 is a front view illustrating the outline of a culture bag storage part used in the cell culture system according to the second embodiment of the present invention, and showing a state in which a medium is not enclosed in a culture bag.
Figure 9:
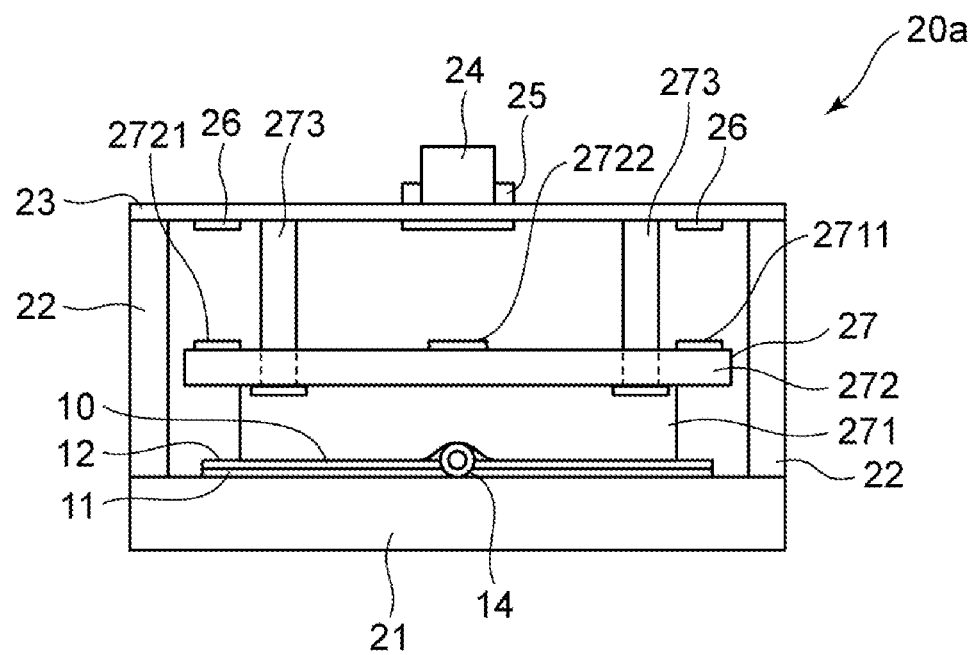
FIG. 9 is a left-side view illustrating the outline of a culture bag storage part used in the cell culture system according to the second embodiment of the present invention, and showing a state in which a medium is not enclosed in a culture bag.

Then, when the medium is completely discharged from the culture bag 10, the culture bag 10 is pressed by the pressing member 27 until the upper surface film and the lower surface film are brought into contact with each other (a plurality of recesses formed in the bottom side film 11 are closed by the top plate side film 12), as shown in FIGS. 8 and 9. At this time, the liquid thickness of the medium in the culture bag 10 is zero.

A sensor support part 24 is fixed to the periphery of the top plate part 23, and the length measurement sensor 25 is attached to the tip thereof. Further, a metal member 2722 is attached to the mounting part 272 of the pressing member 27 so as to face the length measurement sensor 25. The arrangement of the sensor support part 24 and the length measurement sensor 25 is not limited thereto, and they can be attached to the top plate part 23 at any positions within the range in which the distance to the metal member 2722 can be measured.

Then, the distance to the metal member 2722 is measured by the length measurement sensor 25, and the liquid thickness of the medium in the culture bag 10 is calculated, whereby the liquid thickness can be detected.

For example, the liquid thickness can be obtained by multiplying the output voltage of the length measurement sensor 25 by a predetermined coefficient to calculate the distance from the length measurement sensor 25 to the metal member 2722, and subtracting the distance calculated above, the thickness of the metal member 2722, the height of the pressing member, and the thickness of the upper surface film and lower surface film from the distance from the upper surface of the pedestal 21 to the lower surface of the length measurement sensor 25.

The operation of the supply means 30 is controlled by the control part 60 based on detection information from the length measurement sensor 25. At this time, the control part 60 calculates the liquid thickness of the medium in the culture bag 10 based on the output voltage (or output current) input (transferred) from the length measurement sensor 25, and controls the start and stop of the operation of the supply means 30, the rotation speed, and the like based on the liquid thickness, whereby the liquid thickness can be controlled to a desired size.

The control part 60 (control unit) is not particularly limited as long as it can control the operation of the supply means 30 based on detection information from the length measurement sensor 25. The same as the first embodiment can be used.

After the medium is discharged from the culture bag 10 and the output voltage corresponding to the state in which the liquid thickness is zero is stored in the control part 60, the drive of the supply means 30, such as pumps, can be controlled so that the medium in the culture bag 10 has a desired liquid thickness based on detection information from the length measurement sensor 25, thereby supplying the medium to the culture bag 10.

Further, in the present embodiment, it is also possible to provide the length measurement sensor 25 on the pedestal 21 on which the culture bag 10 is placed, and to provide the metal member 2722 on the pressing member 27 to form the culture bag housing part 20a. In another possible configuration, using a weight sensor, the weight including the medium in the culture bag 10 is detected and output to the control part 60, and the control part 60 calculates the liquid thickness of the medium based on the weight of the medium, and controls the operation of the supply means 30.

There are three types of medium supply control in the cell culture system: full-amount exchange, half-amount exchange, and circulating supply.

In the full-amount exchange, the entire medium in the culture bag 10 is discharged to once empty the culture bag 10, then the culture bag 10 is filled again with the medium, and the liquid thickness of the medium in the culture bag 10 is returned to the original liquid thickness.

In the half-amount exchange, half the amount of medium in the culture bag 10 is discharged, then the culture bag 10 is filled again with the medium, and the liquid thickness of the medium in the culture bag 10 is returned to the original liquid thickness.

In the circulating supply, the medium is continuously supplied while maintaining the liquid thickness of the medium in the culture bag 10 within a certain range.

Since the full-amount exchange and the half-amount exchange can be performed by once discharging the medium and then supplying the medium until the medium has a certain liquid thickness, they can be relatively easily controlled.

In contrast, it is difficult to operate the circulating supply stably, and it is necessary to control the supply means 30 in a special way.

For example, if the first supply means and the second supply means are operated at the same time at completely the same supply speed, it is theoretically possible to perform circulating supply while maintaining the liquid thickness.

However, in general, the supply speed of pumps varies, so the liquid thickness changes by the error simply by operating the pumps at the same time.

Therefore, if the pump on the discharge side is faster than the pump on the injection side, the medium is absent in the culture bag 10, and if the pump on the discharge side is slower than the pump on the injection side, there is a risk that the medium in the culture bag 10 may continue to increase to break the bag.

Accordingly, in the cell culture system of the present embodiment, the supply speeds of the medium by the first supply means and the second supply means are controlled to different levels. Of the supply speeds of the medium by the first supply means and the second supply means, the supply speed by the slower supply means is made constant, and the stop and start of the operation of the faster supply means are controlled based on input information from the detection part so that the liquid thickness of the medium in the culture bag 10 is within a certain range, thereby making it possible to operate the circulating supply stably.

Specifically, to start the circulating supply, first, with the medium being absent in the culture bag 10, while stopping the pump on the discharge side, the pump on the injection side is operated at a speed of V, and the filling of the medium is started so that the liquid thickness of the medium in the culture bag 10 becomes, for example, a maximum liquid thickness 3d.

Next, when the liquid thickness of the medium in the culture bag 10 becomes 2d, the pump on the discharge side is operated at a speed of V'. The pump on the injection side remains operated at a speed of V. At this time, as V<V', the speed of the pump on the discharge side is made faster than the speed of the pump on the injection side.

Next, when the liquid thickness of the medium in the culture bag 10 becomes d, the pump on the discharge side is stopped. The pump on the injection side remains operated at a speed of V. As a result, the liquid thickness of the medium in the culture bag 10 increases again to the maximum liquid thickness 3d.

By repeating these operations, the liquid thickness of the medium in the culture bag 10 can be kept within a constant range.

On the contrary, it is also possible to control the stop and start of the operation by making the speed of the pump on the injection side faster than the speed of the pump on the discharge side.

Specifically, first, the culture bag 10 is filled with the medium to the liquid thickness 3d, the pump on the discharge side is operated at a speed of V while stopping the pump on the injection side, and the discharge of the medium is started so that the liquid thickness of the medium in the culture bag 10 becomes d.

Next, when the liquid thickness of the medium in the culture bag 10 becomes d, the pump on the injection side is operated at a speed of V'. The pump on the discharge side remains operated at a speed of V. At this time, as V<V', the speed of the pump on the injection side is made faster than the speed of the pump on the discharge side.

Next, when the liquid thickness of the medium in the culture bag 10 becomes 2d, the pump on the injection side is stopped. The pump on the discharge side remains operated at a speed of V. As a result, the liquid thickness of the medium in the culture bag 10 decreases to d again.

By repeating these operations, the liquid thickness of the medium in the culture bag 10 can be kept within a constant range.

It is also possible to operate the pump on the injection side at a speed of V', operate the pump on the discharge side at a speed of V, make the speed of the pump on the injection side faster than the speed of the pump on the discharge side as V<V', and stop each of them when the liquid thickness of the medium in the culture bag 10 reaches a certain value based on input information from the detection part.

However, with such a configuration, the start (pump motor ON) and stop (pump motor OFF) of the operation of the pump are frequently repeated. Thus, since the motor for moving the pump is damaged, although control is possible, the above control is more preferable.

According to such a cell culture system of the present embodiment, the liquid thickness of the medium in the culture bag can be grasped, whereby it is possible to grasp the amount of medium remaining in the culture bag.

In addition, the timing of contact between the upper surface film and lower surface film of the culture bag can be grasped. This makes it possible to prevent the absence of the medium in the culture bag. It is also possible to detect supply errors caused by pump failure or improper installation.

Furthermore, it is also possible to suitably perform circulating supply of the medium in the cell culture system by controlling the operation of the supply means.

In addition, it is also possible to control the width of the gap between the upper surface film and the lower surface film having a plurality of recesses of the culture bag to a size that does not allow the movement of spheres (a gap of about 50 μm), thereby preventing the movement of the spheres between the recesses.

Third Embodiment

Next, the third embodiment of the cell culture system according to the present invention will be described with reference to FIG. 10.

Figure 10:
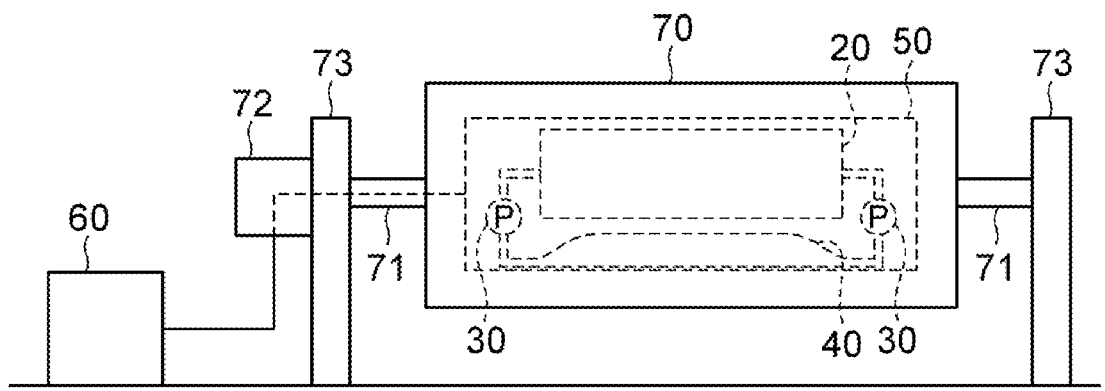
FIG. 10 is an explanatory diagram illustrating the structure of a cell culture system according to a third embodiment of the present invention.

As shown in FIG. 10, the cell culture system of this embodiment comprises a housing 70 that stores a culture unit 50, a rod-like member 71 protruding from a side wall of the housing 70, a drive part 72 that rotates the housing 70 along the central axis of the rod-like member 71, and a support mechanism 73 that rotatably supports the housing 70. The other structures can be the same as those of the first embodiment or the second embodiment, except for the points described below.

In the present embodiment, it is preferable to use tube pumps as the supply means 30, and to provide the supply means 30 in each of the tubular members 14 connected to a plurality of ports 13 provided in the culture bag 10.

Because the supply means 30 are provided in this way, for example, when the culture bag 10 is pressed by a pressing member, the backflow of the medium to the medium bag 40 due to the pressure of the pressing member can be prevented.

Moreover, for example, even if air bubbles are generated in the tubular member 14 connected to the culture bag 10, the supply means 30 can be operated to transfer the air bubbles to the medium bag 40 and discharge them.

Furthermore, even if the culture bag 10 is rotated to change its posture, sudden pressure fluctuations in the culture bag 10 can be prevented without the influence from the hydraulic head difference, and it is possible to eliminate the negative impact on cells.

In the present embodiment, the housing 70 fixes and holds the culture bag storage part 20, the supply means 30, the tubular members 14, and the medium bag 40 in the culture unit 50. The arrangement thereof in the housing 70 is not particularly limited, and the fixing method thereof is also not limited.

The rod-like member 71 is a rotating shaft for rotating the housing 70, and may be formed separately from the housing 70 and fixed to the housing 70, or may be formed integrally with the housing 70. The rod-like member 71 can be formed into a cylindrical shape and wiring cords connected to the input/output part 61 of the control part 60 can be connected to the supply means 30 and the length measurement sensor 25 through the inside thereof.

The drive part 72 rotates the rod-like member 71 along its central axis to thereby rotate the housing 70. The drive part 72 is connected to the input/output part 61 of the control part 60 through a wiring cord, and can be controlled by the control part 60. Further, other control parts may be used to control the drive part 72.

The support mechanism 73 supports the rod-like member 71 to thereby rotatably support the housing 70.

According to such a cell culture system of the present embodiment, the medium can be supplied to the culture bag 10 even when the culture bag 10 is rotated to make the culture part vertical or upside down.

Furthermore, for example, when adherent cells are cultured by attaching them to the culture part of the culture bag 10, the adherent cells are attached to the lower surface side of the culture bag 10, the culture bag 10 is then inverted upside down to attach the adherent cells to the original upper surface side (new lower surface side) of the culture bag 10, and the cells are cultured by inverting the culture bag 10 upside down, as appropriate, thereby making it possible to double the culture area.

In addition, after controlling the liquid thickness of the medium to a size that does not allow the movement of the spheres, the culture bag 10 is inverted upside down, thereby making it possible to discharge dead cells and the medium while holding the spheres in recesses formed in the culture part of the culture bag 10, and to suitably perform full-amount exchange or half-amount exchange.

Fourth Embodiment

Next, the fourth embodiment of the cell culture system according to the present invention will be described with reference to FIG. 11.

Figure 11:
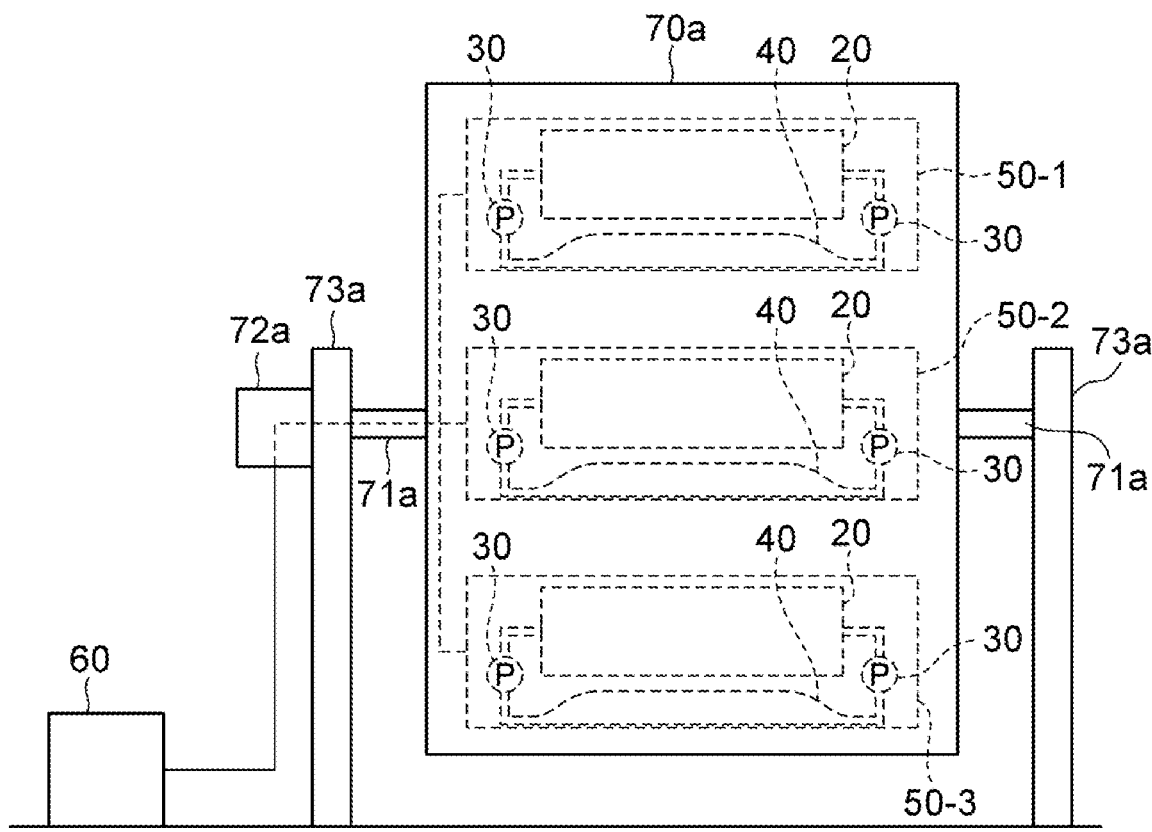
FIG. 11 is an explanatory diagram illustrating the structure of a cell culture system according to a fourth embodiment of the present invention.

As shown in FIG. 11, the cell culture system of this embodiment comprises a second housing 70a in which a plurality of culture units 50 (50-1, 50-2, and 50-3) are stored (laminated), a second rod-like member 71a protruding from a side wall of the second housing 70a, a second drive part 72a that rotates the second housing 70a along the central axis of the second rod-like member 71a, and a second support mechanism 73a that rotatably supports the second housing 70a. The other structures can be the same as those of the third embodiment, except for the points described below.

The housing 70a fixes and holds the culture bag storage part 20, the supply means 30, the tubular members 14, and the medium bag 40 in each of the culture units 50.

The rod-like member 71a is a rotating shaft for rotating the housing 70a, and may be formed separately from the housing 70a and fixed to the housing 70a, or may be formed integrally with the housing 70a. The rod-like member 71a can be formed into a cylindrical shape and wiring cords connected to the input/output part 61 of the control part 60 can be connected to the supply means 30 and the length measurement sensor 25 through the inside thereof.

The drive part 72a rotates the rod-like member 71a along its central axis to thereby rotate the housing 70a. The drive part 72a is connected to the input/output part 61 of the control part 60 through a wiring cord, and can be controlled by the control part 60. Further, other control parts may be used to control the drive part 72a.

The support mechanism 73a supports the rod-like member 71a to thereby rotatably support the housing 70a.

According to such a cell culture system of the present embodiment, in addition to the effects of the third embodiment, the use of a plurality of culture bags 10 can increase the culture area, and the inflow and discharge of the medium to each culture bag 10 can be finely controlled, thereby making it possible to culture a large amount of cells.

Fifth Embodiment

Next, the fifth embodiment of the cell culture system according to the present invention will be described with reference to FIG. 12.

In the cell culture system of this embodiment, a plurality of culture bags are connected in parallel to one medium container (medium bag 40) by tubular members, and one supply means is provided in each tubular member that connects each branched portion in the tubular member and the ports of the plurality of culture bags. The other structures can be the same as those of the cell culture system of the first embodiment, except for the points described below.

Figure 12:
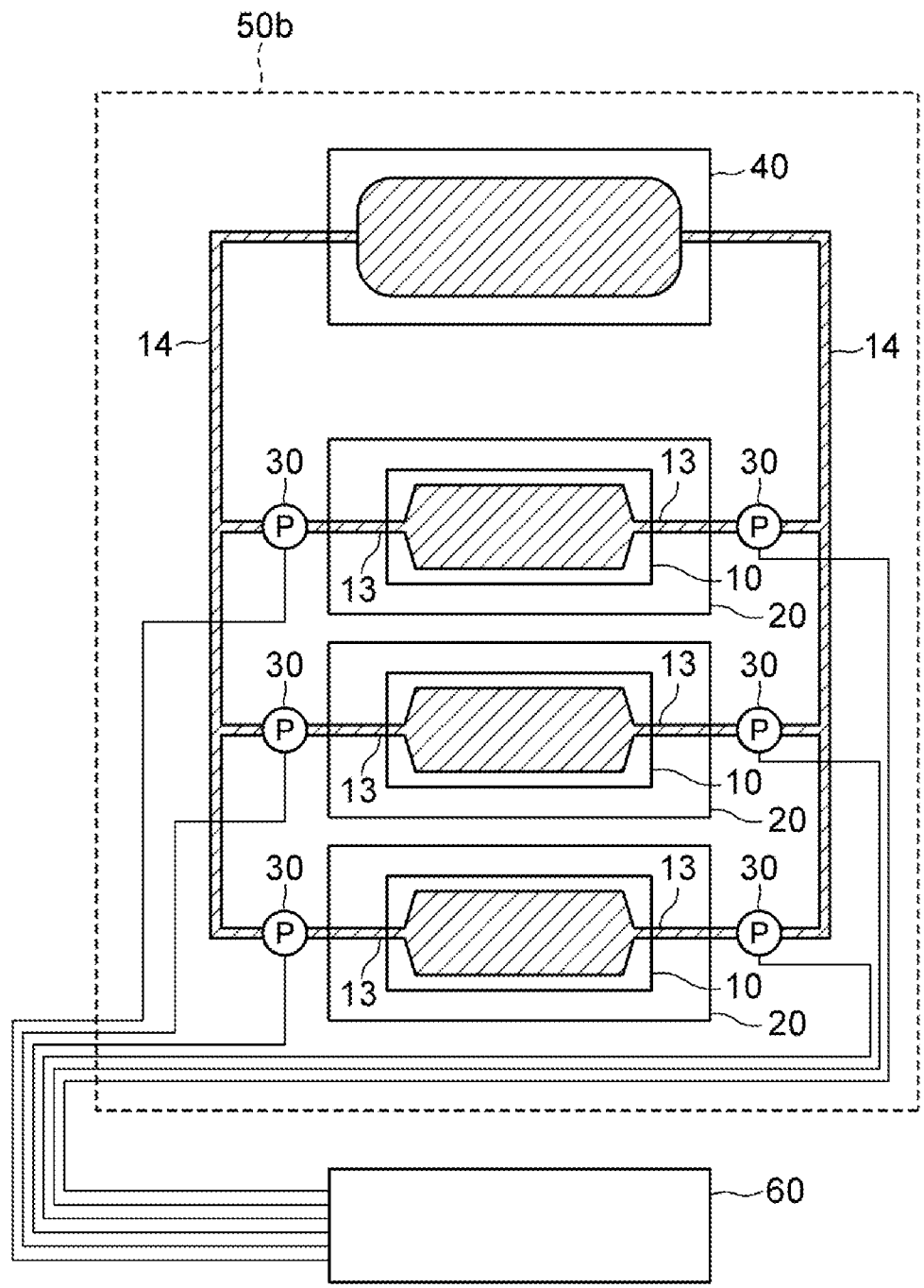
FIG. 12 is an explanatory diagram illustrating the structure of a cell culture system according to a fifth embodiment of the present invention.

In FIG. 12, the culture bags 10 are each provided with two ports 13. These ports 13 are each connected to a tubular member 14, and each tubular member 14 is connected to other culture bags 10 and the medium bag 40. Further, the tubular members 14 are each partially branched and connected to the culture bags 10 and the medium bag 40.

The tubular members 14 on both sides of each port of the culture bag 10 are each provided with supply means 30. In this case, one supply means 30 is provided in each tubular member 14 that connects a certain branched portion in the tubular member 14 and the port 13 of the culture bag 10. Tube pumps are preferably used as the supply means 30.

The input/output part 61 of the control part 60 is connected to each supply means 30 by wiring cords. Then, the operation of these supply means 30 is controlled based on instruction information from PLC 62. These supply means 30 can be separately controlled.

Further, it is also preferable that the cell culture system of the present embodiment is configured to comprise a second culture unit (a multiply-connected culture unit in which a plurality of culture bags are connected to a common medium container) 50b having a plurality of culture bag storage parts 20 each comprising a pedestal on which a culture bag 10 is placed, a pressing member that presses the culture bag 10 against the pedestal to thereby uniformize the liquid thickness in the culture bag 10, a top plate part provided to face the pressing member, and a support mechanism that supports the pressing member movably in the vertical direction with respect to the top plate part; a medium container storage part (not shown) that stores a medium bag 40; and a storage part (not shown) that stores each supply means 30 and tubular members 14 that connect the plurality of culture bags 10 and the medium bag 40.

When the cell culture system of the present embodiment is configured as described above, it is possible to suitably control the supply of the medium in each culture bag 10.

In the case of connecting a plurality of culture bags 10 to a common medium bag 40, for example, if a pump was provided in only one of the tubular members 14 connected to the culture bag 10 having two ports, or if a solenoid valve was provided in both tubular members 14, most of the medium flowed in the easy-to-flow one among the branched tubular members 14, which caused a problem that the medium could not be uniformly supplied to each culture bag 10.

In contrast, according to the cell culture system of the present embodiment, each of the tubular members 14 at both sides of each port of the culture bag 10 is provided with a pump as the supply means 30, and the operation of these supply means 30 can be controlled, whereby it is possible to uniformly supply the medium to the plurality of culture bags 10.

Moreover, according to the cell culture system of the present embodiment, even when using a medium bag 40 common to a plurality of culture bags 10, the operation of each supply means 30 can be controlled separately, whereby it is possible to separately and finely control the supply of the medium to each culture bag 10.

Furthermore, since culture can be suitably performed using a plurality of culture bags 10 in this way, it is possible to culture a large amount of cells.

Sixth Embodiment

Next, the sixth embodiment of the cell culture system according to the present invention will be described with reference to FIG. 13.

The cell culture system of this embodiment is different from the cell culture system of the fifth embodiment in that it comprises a detection part that measures a change occurring in response to a change in the amount of medium in the culture bag, and the operation of each supply means is controlled based on detection information input from the detection part, as with the second embodiment. The other structures can be the same as those of the fifth embodiment, except for the points described below.

Figure 13:
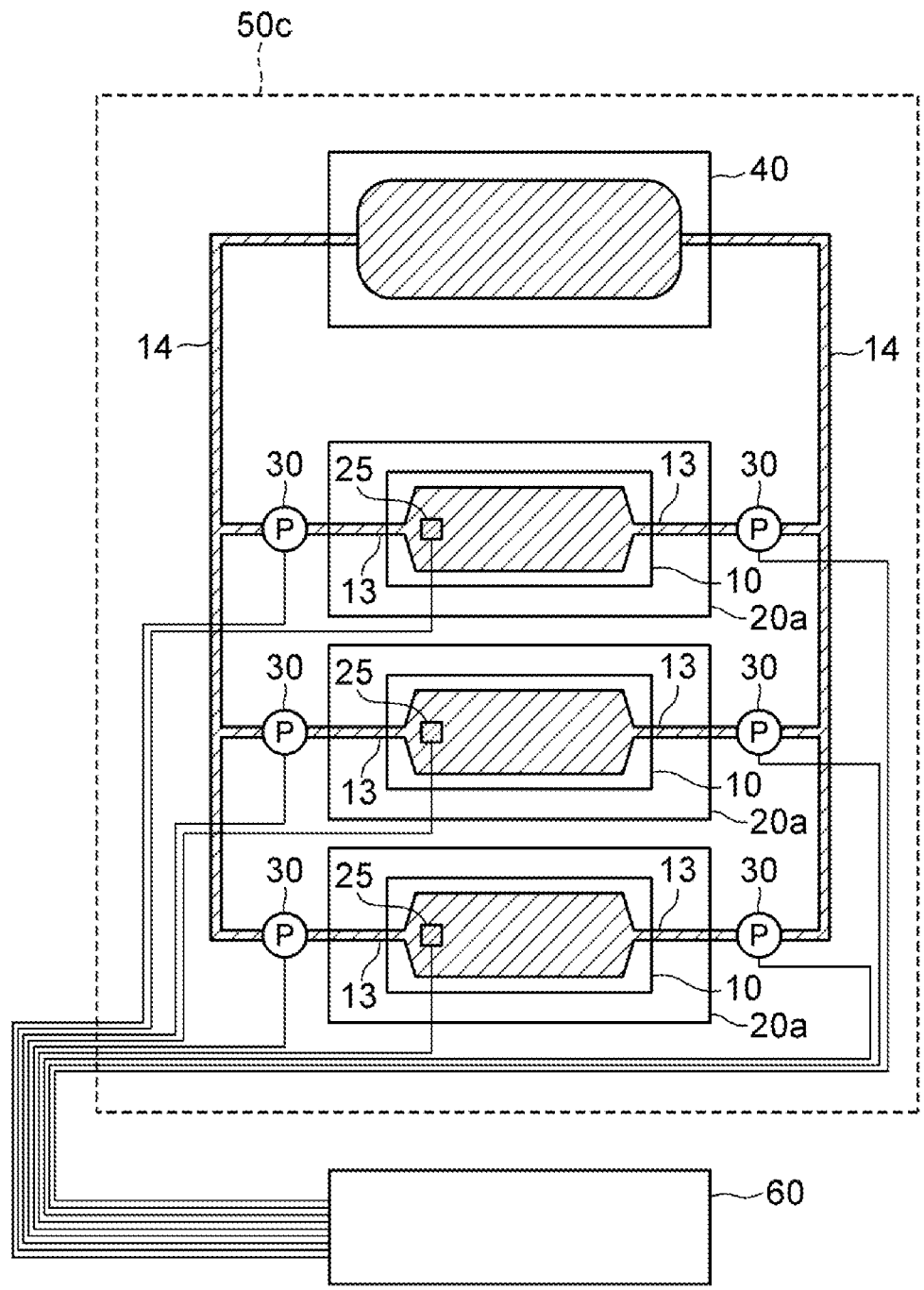
FIG. 13 is an explanatory diagram illustrating the structure of a cell culture system according to a sixth embodiment of the present invention.

In FIG. 13, the input/output part 61 of the control part 60 is connected to each supply means 30 by wiring cords. The input/output part 61 is also connected to each length measurement sensor 25 by wiring cords. Then, the control part 60 can separately control the operation of each supply means 30 corresponding to (provided in the same culture bag 10) each length measurement sensor 25 based on detection information from each length measurement sensor 25.

For example, the control part 60 calculates the liquid thickness of the medium in the culture bag 10 based on the output voltage etc. input from the length measurement sensor 25, and controls the start and stop of the operation of the supply means 30, the rotation speed, and the like based on the liquid thickness, whereby the liquid thickness can be controlled to a desired size.

Further, it is also preferable that the cell culture system of the present embodiment is configured to comprise a third culture unit (a multiply-connected culture unit having length measurement sensors, in which a plurality of culture bags are connected to a common medium container) 50c having a plurality of culture bag storage parts 20a each comprising a pedestal on which a culture bag 10 is placed, a pressing member that presses the culture bag 10 against the pedestal to uniformize the liquid thickness in the culture bag 10, a top plate part provided to face the pressing member, a support mechanism that supports the pressing member movably in the vertical direction with respect to the top plate part, and a length measurement sensor; a medium container storage part (not shown) that stores a medium bag 40; and a storage part (not shown) that stores each supply means 30 and tubular members 14 that connect the plurality of culture bags 10 and the medium bag 40.

When the cell culture system of the present embodiment is configured as described above, in addition to the effects of the cell culture system of the fifth embodiment, it is possible to more finely control the supply of the medium in the culture bags 10, and further to control the liquid thickness of the medium in the culture bags 10.

Seventh Embodiment

Next, the seventh embodiment of the cell culture system according to the present invention will be described with reference to FIG. 14.

Figure 14:
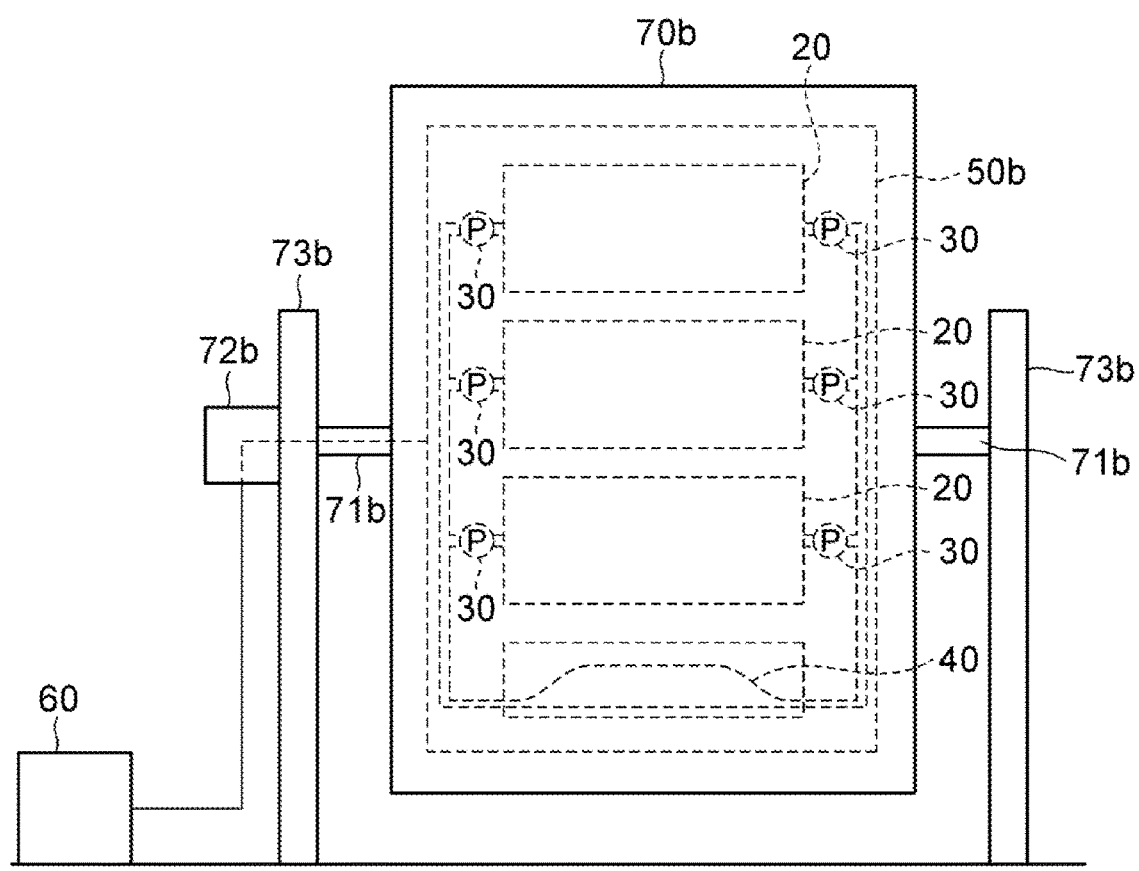
FIG. 14 is an explanatory diagram illustrating the structure of a cell culture system according to a seventh embodiment of the present invention.

As shown in FIG. 14, the cell culture system of this embodiment comprises a third housing 70b that stores multiply connected culture units (50b and 50c), a third rod-like member 71b protruding from a side wall of the third housing 70b, a third drive part 72b that rotates the third housing 70b along the central axis of the third rod-like member 71b, and a third support mechanism 73b that rotatably supports the third housing 70b. The other structures can be the same as those of the fifth embodiment or the sixth embodiment, except for the points described below.

The housing 70b fixes and holds the culture bag storage part 20, the supply means 30, the tubular members 14, and the medium bag 40 in each of the multiply connected culture units (50b and 50c).

The rod-like member 71b is a rotating shaft for rotating the housing 70b, and may be formed separately from the housing 70b and fixed to the housing 70b, or may be formed integrally with the housing 70b. The rod-like member 71b can be formed into a cylindrical shape and wiring cords connected to the input/output part 61 of the control part 60 can be connected to the supply means 30 and the length measurement sensor 25 through the inside thereof.

The drive part 72b rotates the rod-like member 71b along its central axis to thereby rotate the housing 70b. The drive part 72b is connected to the input/output part 61 of the control part 60 through the wiring cord, and can be controlled by the control part 60. Further, other control parts may be used to control the drive part 72b.

The support mechanism 73b supports the rod-like member 71b to thereby rotatably support the housing 70b.

According to such a cell culture system of the present embodiment, when using a medium bag 40 common to a plurality of culture bags 10, the medium can be appropriately supplied to each culture bag 10 even when the culture bags 10 are rotated to make the culture parts vertical or upside down.

Eighth Embodiment

Figure 15:
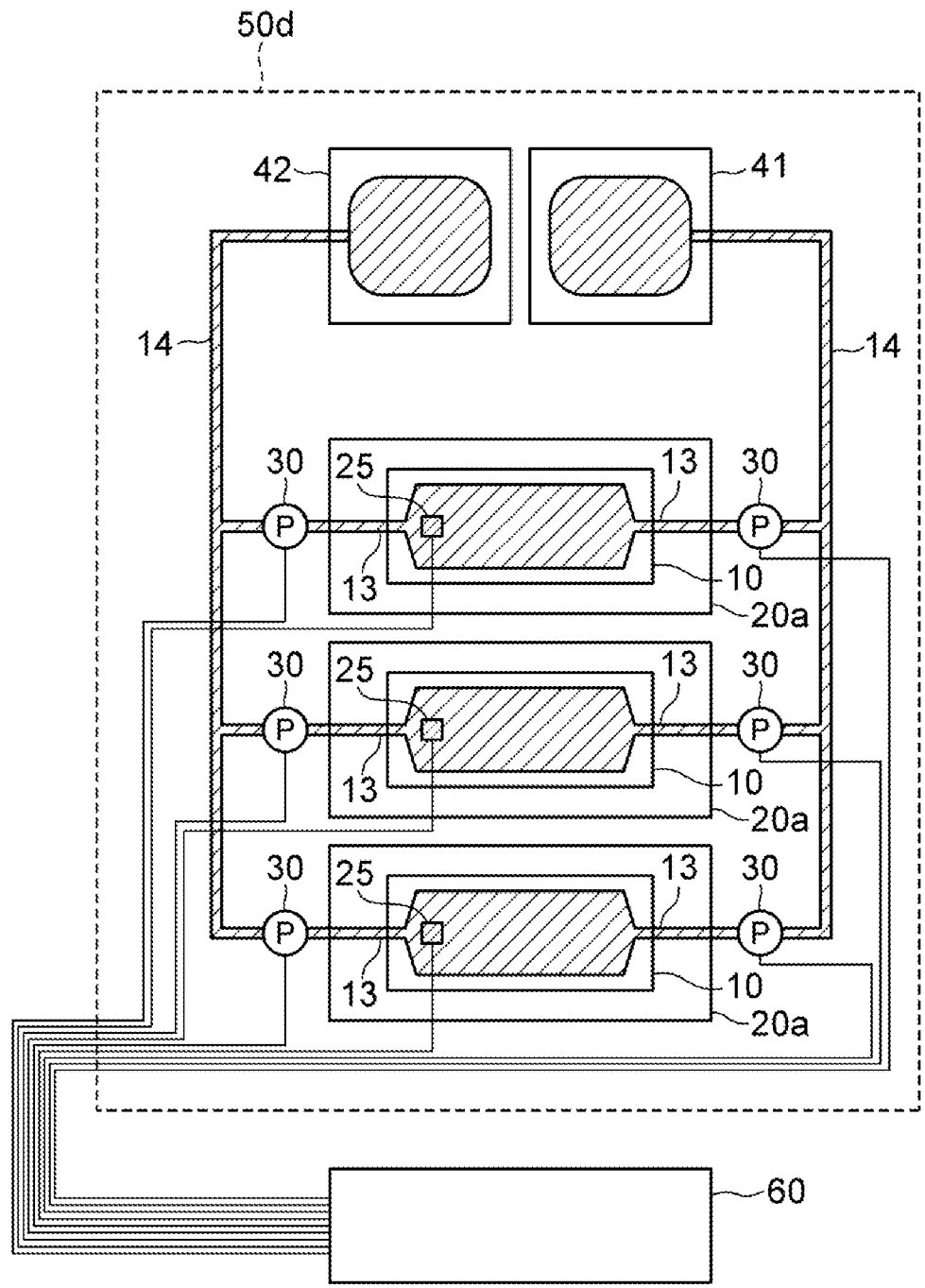
FIG. 15 is an explanatory diagram illustrating the structure of a cell culture system according to an eighth embodiment of the present invention.

Next, the eighth embodiment of the cell culture system according to the present invention will be described with reference to FIG. 15.

The cell culture system of this embodiment comprises a plurality of culture bags made of a flexible packaging material and each having a plurality of ports, a first medium container that stores a medium to be transferred to the plurality of culture bags, a second medium container that stores the medium transferred from the plurality of culture bags, and a control part that controls the supply of the medium, tubular members are connected to the respective ports, and the plurality of culture bags are connected to the first medium container and the second medium container by the tubular members, the tubular members that connect branched portions in the tubular members and the ports of the plurality of culture bags are each provided with one supply means, and the control part controls the operation of each supply means to control the transfer of the medium in the plurality of culture bags, the first medium container, and the second medium container.

That is, in the cell culture system of the present embodiment, the medium is supplied from a first medium container 41 to each culture bag 10, and supplied from each culture bag 10 to a second medium container 42, without circulation.

The liquid thickness of the medium in the culture bags 10 can also be finely and appropriately controlled by such a cell culture system of the present embodiment, as in the cell culture system of the sixth embodiment.

Moreover, the length measurement sensor 25 can be omitted from the culture bag storage part 20a in the cell culture system of the present embodiment. The supply of the medium in the culture bags 10 can also be suitably controlled by such a cell culture system, as in the cell culture system of the fifth embodiment.

Furthermore, the cell culture system of the present embodiment can be combined with the cell culture system of the seventh embodiment so that the medium can be appropriately supplied to each of the plurality of culture bags 10 even when the culture bags 10 are rotated to make the culture parts vertical or upside down.

It is also preferable that the culture bag used in the cell culture system of the present embodiment is configured such that in the top plate side film 12, top plate protrusion portions are provided on the inside of the culture bag 10, the width of the top plate protrusion portions is smaller than the width of openings of recesses formed in the bottom side film 11, and the height of the top plate protrusion portions is smaller than the minimum diameter of the culture target, so that when the top plate protrusion portions are brought into contact with a part of the upper end surface of the culture part, a gap is formed between the upper end surface and the lower surface of the top plate side film 12.

When the culture bag used in the cell culture system of the present embodiment is configured as described above, the top plate protrusion portions can be brought into contact with a part of the upper end surface to form a gap, which is smaller than the size of the culture target, between the upper end surface and the top plate part. This makes it possible to prevent the movement of the culture target, such as spheres, while allowing liquids, such as the medium, to pass through the gap.

When the culture target is spheres, the culture system of the present embodiment can be used in, for example, a step of forming spheres, a step of culturing cells to grow while maintaining the sphere state, and a step of inducing the differentiation of cells in the sphere state.

The culture system of the present embodiment can also be used in, for example, a method of forming spheres using differentiated cells obtained from iPS cells, ES cells, and other stem cells by differentiation induction, or a method of once cryopreserving differentiated cells, thawing them again, and then forming spheres.

As described above, according to the cell culture system of the embodiment of the present invention, the inflow and discharge of the medium from the medium container to the culture bag can be finely controlled.

Moreover, by grasping the liquid thickness of the medium in the culture bag, it is possible to grasp the amount of medium remaining in the culture bag, and the timing of contact between the upper surface film and the lower surface film of the culture bag. It is possible to prevent the absence of the medium in the culture bag, and to detect supply errors caused by pump failure or improper installation.

Furthermore, it is possible to supply the medium to the culture bag even when the culture bag is rotated to make the culture part vertical or upside down. For example, when adherent cells are cultured by attaching them to the culture part of the culture bag, it is possible to double the culture area by inverting the culture bag upside down, as appropriate.

In addition, due to the use of a plurality of culture bags, the culture area can be increased, and the inflow and discharge of the medium to each culture bag can be finely controlled. Therefore, it is possible to culture a large amount of cells.

The present invention is not limited to the above-mentioned embodiments, and it is needless to say that various modifications are possible within the scope of the present invention. It is possible to make changes as needed; for example, the culture bag is provided with three or more ports, pumps are provided in tubular members connected to the ports, and these pumps are controlled based on information from a detector, or the arrangement of the pressing member and the length measurement sensor in the culture bag storage part is changed.

INDUSTRIAL APPLICABILITY

The present invention can be suitably used, for example, for efficiently mass-producing spheres, organoids, and the like with a uniform size.

The documents described in the specification and the Japanese patent application claiming the priority under the Paris Convention to the invention are incorporated herein by reference in its entirety.

DESCRIPTION OF REFERENCE SIGNS

10: Culture bag
11, 11a, 11b: Bottom side film
111, 111a, 111b: Recess
12: Top plate side film
13: Port
14: Tubular member
20, 20a: Culture bag storage part
21: Pedestal
22: Top plate support part
23: Top plate part
231: Top plate opening
24: Sensor support part
25: Length measurement sensor
26: Permanent magnet
27: Pressing member
271: Pressing part
272: Mounting part
2721: Permanent magnet
2722: Metal member
273: Guide pin
30: Supply means
40, 41, 42: Medium bag
50, 50a, 50b, 50c, 50d: Culture unit
60: Control part
61: Input/output part
62: PLC
63: Relay part
64: Operation part
65: Power supply part
66: Wiring interrupting part
70, 70a, 70b: Housing
71, 71a, 71b: Rod-like member
72, 72a, 72b: Drive part
73, 73a, 73b: Support mechanism

The invention claimed is:
1. A cell culture system comprising:
a culture bag made of a flexible packaging material and having first and second ports;
a medium container that stores a medium to be transferred to the culture bag;
a controller that includes a processor, the controller being configured to control a supply of the medium;
a weight sensor or a length measurement sensor that measures a weight or length change, respectively, occurring in response to a change in amount of medium in the culture bag,
first and second tubular members;
first and second pumps;
wherein:
the first and second tubular members are connected to the first and second ports, respectively, to circularly connect the culture bag and the medium container through the first and second tubular members;
the first tubular member connects between the first port and the medium container, and the first pump is disposed in the first tubular member;
the second tubular member connects between the second port and the medium container, and the second pump is disposed in the second tubular member;
the controller is configured to:

calculate a liquid thickness of the medium in the culture bag based on detection information input from the weight sensor or the length measurement sensor, and, based on the liquid thickness of the medium, control an operation of the first pump and the second pump to circulate the medium in the culture bag and the medium container, thereby making the liquid thickness in the culture bag within a certain range.

2. The cell culture system according to claim 1, wherein the first pump and the second pump are tube pumps.

3. The cell culture system according to claim 1, wherein the controller is configured to control the first pump and the second pump, such that the first pump supplies the medium with a supply speed faster than the second pump.

4. The cell culture system according to claim 3, wherein the controller is configured to control the first pump and the second pump, such that the supply speed of the second pump is kept constant, and stop and start of the operation of the first pump based on input information from the weight sensor or the length measurement sensor, thereby making the liquid thickness of the medium in the culture within the certain range.

5. The cell culture system according to claim 1, comprising a culture unit, wherein the culture unit comprises:

a culture bag storage part comprising a pedestal on which the culture bag is placed, a pressing member that presses the culture bag against the pedestal to uniformize the liquid thickness in the culture bag, a top plate part that is provided to face the pressing member, and a support mechanism that supports the pressing member movably in a vertical direction with respect to the top plate part;

a medium container storage part that stores the medium container; and a storage part that stores the first and second tubular members that connect the culture bag and the medium container.

6. The cell culture system according to claim 5, wherein the weight sensor or the length measurement sensor that measures a weight or length change, respectively, occurring in response to a change in amount of medium in the culture bag comprises the length measurement sensor and the length measurement sensor is disposed on the top plate part, and the length measurement sensor measures a distance to a metal member disposed on the pressing member.

7. The cell culture system according to claim 5, comprising a housing that stores the culture unit, a rod-like member protruding from a side wall of the housing, a drive part that rotates the housing along a central axis of the rod-like member, and the support mechanism that rotatably supports the housing.

8. The cell culture system according to claim 1, further comprising:

additional culture bags connected to the medium container by additional tubular members branched from the first tubular member and the second tubular member, respectively; and additional pumps disposed in the additional tubular members, respectively.

9. The cell culture system according to claim 1, wherein the first port and the second port are arranged point symmetrically with respect to a center of a culture part at both ends of the culture bag.

* * * * *